(12) United States Patent
Fedegari

(10) Patent No.: US 11,892,357 B2
(45) Date of Patent: Feb. 6, 2024

(54) SYSTEM FOR MEASURING THE TEMPERATURE IN A SEVERE ATMOSPHERE ENVIRONMENT, RECEPTION ANTENNA

(71) Applicant: FEDEGARI AUTOCLAVI S.P.A., Albuzzano (IT)

(72) Inventor: Paolo Fedegari, Celerina/Schlarigna (CH)

(73) Assignee: FEDEGARI AUTOCLAVI S.P.A., Albuzzano (IT)

(*) Notice: Subject to any disclaimer, the term of this patent is extended or adjusted under 35 U.S.C. 154(b) by 805 days.

(21) Appl. No.: 17/041,388

(22) PCT Filed: Apr. 16, 2019

(86) PCT No.: PCT/IB2019/053106
§ 371 (c)(1),
(2) Date: Sep. 24, 2020

(87) PCT Pub. No.: WO2019/202484
PCT Pub. Date: Oct. 24, 2019

(65) Prior Publication Data
US 2021/0108969 A1  Apr. 15, 2021

(30) Foreign Application Priority Data
Apr. 17, 2018  (IT) .................. 102018000004603

(51) Int. Cl.
*G01K 1/02* (2021.01)
*G01K 1/08* (2021.01)
(Continued)

(52) U.S. Cl.
CPC ............... *G01K 1/024* (2013.01); *A61L 2/06* (2013.01); *A61L 2/26* (2013.01); *G01K 1/026* (2013.01);
(Continued)

(58) Field of Classification Search
CPC .......... G01K 1/024; G01K 1/026; G01K 1/08; G01K 2215/00; A61L 2/06; A61L 2/26;
(Continued)

(56) References Cited

U.S. PATENT DOCUMENTS

2005/0125105 A1  6/2005  Halstead et al.
2010/0041346 A1  2/2010  Chen et al.
(Continued)

FOREIGN PATENT DOCUMENTS

CN  1278959 A  1/2001
CN  201263147 Y  6/2009
(Continued)

OTHER PUBLICATIONS

Machine translation for CN-104848952 A (Year: 2023).*
(Continued)

*Primary Examiner* — Huy Tram Nguyen
(74) *Attorney, Agent, or Firm* — Steinfl + Bruno LLP

(57) ABSTRACT

A system for measuring temperature in a sterilization autoclave, including a temperature transducer positionable inside a sterilization chamber of the autoclave and a receiver positionable outside the sterilization chamber. The receiver includes a reception antenna and a receiving electronic circuit connectable with a process controller of the autoclave. The receiving electronic circuit is configured to receive a temperature signal through the reception antenna, provide a control signal as a function of the temperature signal, and transmit the control signal to the process controller. The temperature transducer includes a hermetically closable transducer housing, temperature probes, a transmission antenna, an electronic transduction circuit, and a primary battery. The reception antenna of the receiving device is configured to transmit signals at two or more different frequencies.

9 Claims, 5 Drawing Sheets

(51) Int. Cl.
*H04K 3/00* (2006.01)
*A61L 2/06* (2006.01)
*G01K 1/024* (2021.01)
*A61L 2/26* (2006.01)

(52) U.S. Cl.
CPC ............ *G01K 1/08* (2013.01); *A61L 2202/14* (2013.01); *G01K 2215/00* (2013.01); *H04K 3/224* (2013.01)

(58) Field of Classification Search
CPC .......... A61L 2202/14; A61L 2/28; A61L 2/07; H04K 3/224; H04K 3/228; H04K 3/68
USPC ....................................................... 422/119
See application file for complete search history.

(56) References Cited

U.S. PATENT DOCUMENTS

| | | | |
|---|---|---|---|
| 2014/0219142 A1 | 8/2014 | Schulz et al. | |
| 2017/0328196 A1 | 11/2017 | Shi et al. | |
| 2017/0348452 A1 | 12/2017 | Kuzelka | |
| 2021/0052759 A1 | 2/2021 | Fedegari | |

FOREIGN PATENT DOCUMENTS

| | | | |
|---|---|---|---|
| CN | 202269371 U | 6/2012 | |
| CN | 104107448 A | 10/2014 | |
| CN | 104470549 A | 3/2015 | |
| CN | 104483036 A | 4/2015 | |
| CN | 204468769 U | 7/2015 | |
| CN | 204480077 U | 7/2015 | |
| CN | 104848952 A | 8/2015 | |
| CN | 205373900 U | 7/2016 | |
| CN | 205729826 U | 11/2016 | |
| CN | 106817134 A | 6/2017 | |
| CN | 107072748 A | 8/2017 | |
| CN | 206603943 U | 11/2017 | |
| CN | 107449466 A | 12/2017 | |
| DE | 102008021490 A1 | 11/2009 | |
| KR | 20150138960 A | 12/2015 | |
| WO | 2019/202485 A1 | 10/2019 | |

OTHER PUBLICATIONS

Machine translation for CN-205373900 U (Year: 2023).*
Machine translation for DE-102008021490 A1 (Year: 2023).*
Machine translation for CN-1278959 A (Year: 2023).*
First Chinese Office Action for CN Application No. 201980025721.9 filed on Apr. 16, 2019 on behalf of Fedegari Autoclavi S.P.A. dated Oct. 22, 2021 15 pages (English + Original).
First Chinese Office Action for CN Application No. 201980025728.0 filed on Apr. 16, 2019 on behalf of Fedegari Autoclavi S.P.A. dated Oct. 25, 2021 19 pages (English + Original).
Ellab—TrackSense Pro, "The Ultimate Wireless Data Logger" *Ellab Validation Solutions*, Publication Date: Mar. 13, 2018, Retrieved Dec. 11, 2018, pp. 1-16.
FasintFasLab: "Fasinternational Ha Testato I Sistemi Di Convalida Ellab Nel Fedegari Tech Center", Uploaded Mar. 10, 2017, 1 page, https://www.youtube.com/watch?time_continue=9&v=XKJsulZd1Qk, [retrieved on Dec. 11, 2018].
International Search Report for PCT/IB2019/053106 filed on Apr. 16, 2019 on behalf of Fedegari Autoclavi S.P.A. dated Jul. 11, 2019 5 pages.
International Search Report for PCT/IB2019/053107 filed on Apr. 16, 2019 on behalf of Fedegari Autoclavi S.P.A. dated Jul. 12, 2019 5 pages.
Written Opinion for PCT/IB2019/053106 filed on Apr. 16, 2019 on behalf of Fedegari Autoclavi S.P.A. dated Jul. 11, 2019 9 pages.
Written Opinion for PCT/IB2019/053107 filed on Apr. 16, 2019 on behalf of Fedegari Autoclavi S.P.A. dated Jul. 12, 2019 10 pages.
Indian Office Action for IN Application No. 202027038966 filed on Sep. 9, 2020 on behalf of Fedegari Autoclavi S.P.A. dated Jul. 26, 2022 5 pages.

* cited by examiner

SYSTEM FOR MEASURING THE TEMPERATURE IN A SEVERE ATMOSPHERE ENVIRONMENT, RECEPTION ANTENNA

CROSS-REFERENCE TO RELATED APPLICATIONS

The present application is the U.S. National Stage of International Patent Application No. PCT/IB2019/053106 filed on Apr. 16, 2019 which, in turn, claims priority to Italian Patent Application No. IT 102018000004603 filed on Apr. 17, 2018.

TECHNICAL FIELD

The present invention relates to an improved system for measuring the temperature in a severe atmosphere environment, in particular inside a sterilisation autoclave for sterilising objects and substances. In particular, the present invention relates to an improved reception antenna that can be positioned in a receiver of the system for measuring the temperature.

BACKGROUND ART

With particular reference to the medical or chemical/pharmaceutical field, it is common practice to sterilise every medical device. This operation takes place with different methods according to the type of materials and devices to be sterilised and is codified by strict standards that aim to protect the health and guarantee the safety of patients, hospital workers and the environment.

A commonly used sterilisation process envisages the exposure of objects to substances to be sterilised at temperatures in the range between +120° C. and +140° C. through superheated steam, along with a possible baric treatment at pressure greater than or equal to ambient pressure (e.g. between −2 and 6 bar, preferably between 0 and 3 bar absolute), inside so-called stainless steel autoclaves. To facilitate the loading and unloading operations of the objects or substances to be sterilised, stainless steel pallets are provided which allow the simultaneous stacking and treatment (insertion in the autoclave, sterilisation and removal from the autoclave) of a plurality of objects and substances subjected to the same sterilisation cycle.

Some known sterilisation processes are controlled as a function of the pressure inside the sterilisation chamber and "validated" through a temperature measurement that confirms or not the reaching of the required temperature.

For such temperature measurement the use of resistance thermometers or RTDs (Resistance Temperature Detectors) is known, which exploit the variation of the resistivity of some materials as the temperature changes. Such thermal probes must be positioned in the space of the sterilisation chamber that contains the objects to be sterilised (the positioning of the thermal probes depends on the distribution of the objects inside the sterilisation chamber) and can comprise an electrical cable for connection with a control unit of the autoclave arranged outside the sterilisation chamber. Other known thermal probes can comprise an antenna for wireless transmission to the control unit of the autoclave.

The temperature constitutes the variable measured by such systems which fundamentally characterises the sterilisation cycle.

Furthermore, some sterilisation processes require the load to be treated to be moved during one or more steps of the treatment such as, for example, rotating loads or loads kept in mechanical movement during the treatment, loads moved, also automatically, on various carriages for the loading into and unloading from the sterilisation chamber, sterilisation tunnels.

For example, the objects or substances to be sterilised are placed on rotatable pallets inside the autoclave. In this case, the placement of the thermal probes in the load requires electrical connections with rotating contacts able to operate reliably in the severe environmental conditions of the autoclave. However, such rotating contacts are structurally complex and very expensive.

The known antennas used in heavy atmosphere, normally operate at a frequency of 2.4 GHz, which, after several tests, proved to be inefficient to ensure optimal communication within the autoclave free of disturbances.

The presence of severe environmental conditions, present inside the sterilization chamber of an autoclave, leads to possible wear and malfunctions of the receiving antennas that face it, and that result in possible losses of the measured temperature data.

The loss of temperature data during the sterilisation cycle can lead to the need to eliminate the treated load, as it cannot be certified with certainty that the legislative parameters have been respected.

A further problem of known systems is the management of the transmission frequencies of the antennas, which may vary from country to country depending on the local regulations in force and/or depending on the design parameters of the system.

Other problem of known systems is that the positioning of the antennas is critical, as they must remain protected from the harsh atmosphere environment and at the same time ensure optimal coverage for the reception/transmission of the signals involved.

Another problem with known antennas for heavy-duty measurement systems is that the use of different frequencies or calibrations requires antenna replacement, resulting in costs and time wastage. In addition, switching from one frequency to another is only achieved by manually intervening on the hardware and reconfiguring the system from time to time.

Another problem of the known systems is that the presence of protective elements of the antenna can involve an alteration of the carrier frequency of transmission or reception, such as to make an antenna commercially available uncalibrated and incompatible with use in harsh atmospheres.

An object of the present invention is therefore that of devising a temperature measuring system in a severe atmosphere environment, in particular inside an autoclave for sterilising objects and substances, having characteristics such as to overcome the mentioned drawbacks with reference to the prior art.

Within the scope of such general object, a particular object of the present invention is that of guaranteeing the best efficiency and reliability of management of the antennas receiving the temperature measurement signals involved.

Another object of the present invention is to allow an optimal protection of the antennas present in the harsh atmosphere environment.

Yet another object of the present invention is that of guaranteeing the ease of use and reliability of the antennae exposed to the severe atmosphere.

DISCLOSURE OF THE INVENTION

This and other objects are reached through a perfected temperature measuring system, according to claim 1.

Advantageous embodiments are the subject matter of the dependent claims.

The invention makes it possible to guarantee optimal and interference-free transmission frequencies.

In addition, it protects the antennas in the harsh atmosphere from wear, corrosion and possible malfunctions, while ensuring the best communication efficiency inside the sterilization chamber.

The invention achieves the following technical effects:
- possibility to select between different transmission frequencies without having to intervene manually on the hardware;
- allows the positioning of more antennas ensuring optimal coverage for the transmission/reception of the signals involved;
- design calibrated to ensure the best communication efficiency of the signals involved;
- simple operation and use.

The technical effects/advantages mentioned, and other technical effects/advantages of the invention will emerge in further detail from the description provided herein below of an example of embodiment provided by way of approximate and non-limiting example with reference to the attached drawings.

DETAILED DESCRIPTION OF PREFERRED EMBODIMENTS OF THE INVENTION

Figure 1:
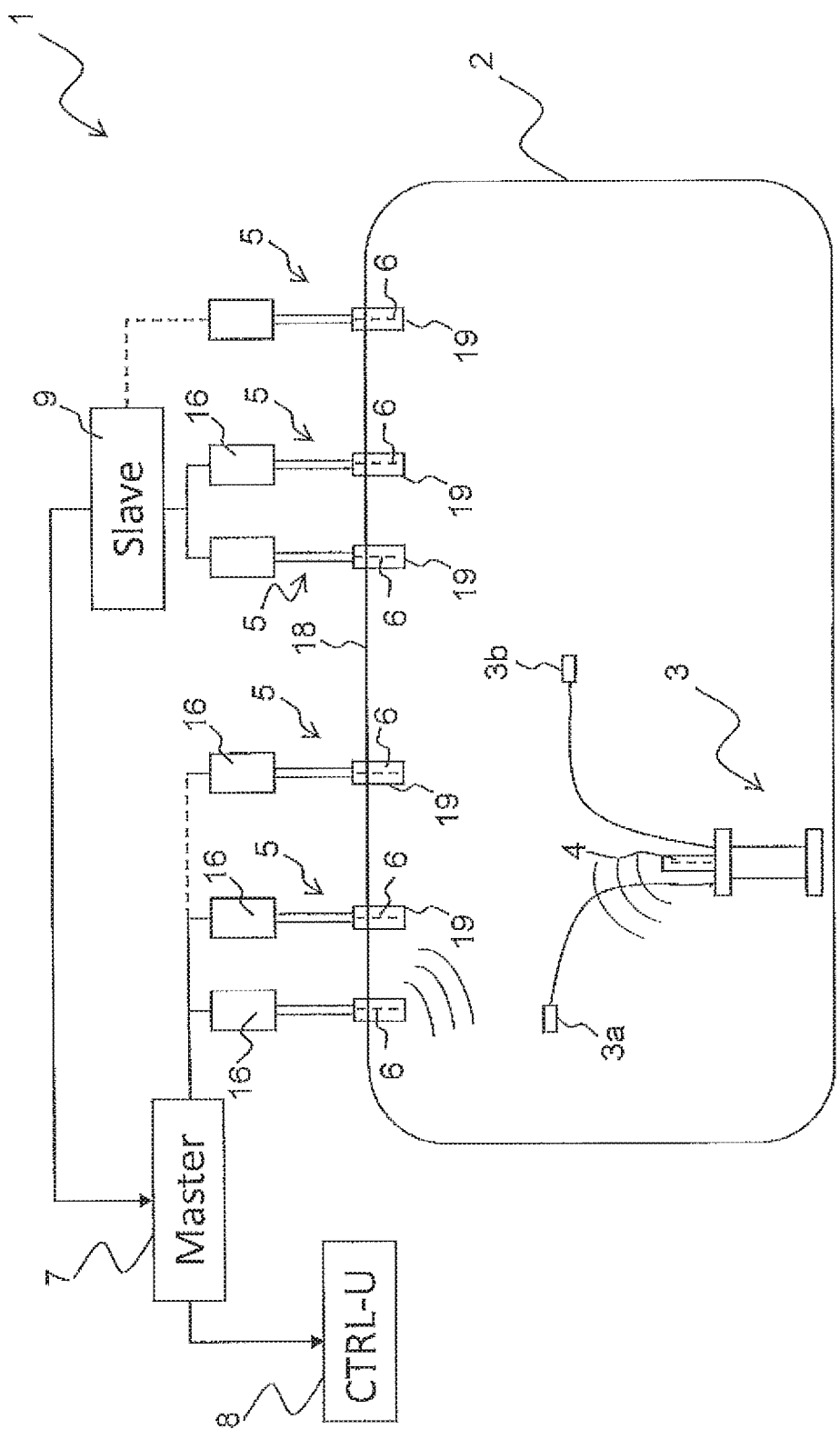
FIG. 1 is a schematic view of the architecture of the temperature measuring system inside a sterilisation chamber according to the invention.
Figure 2:
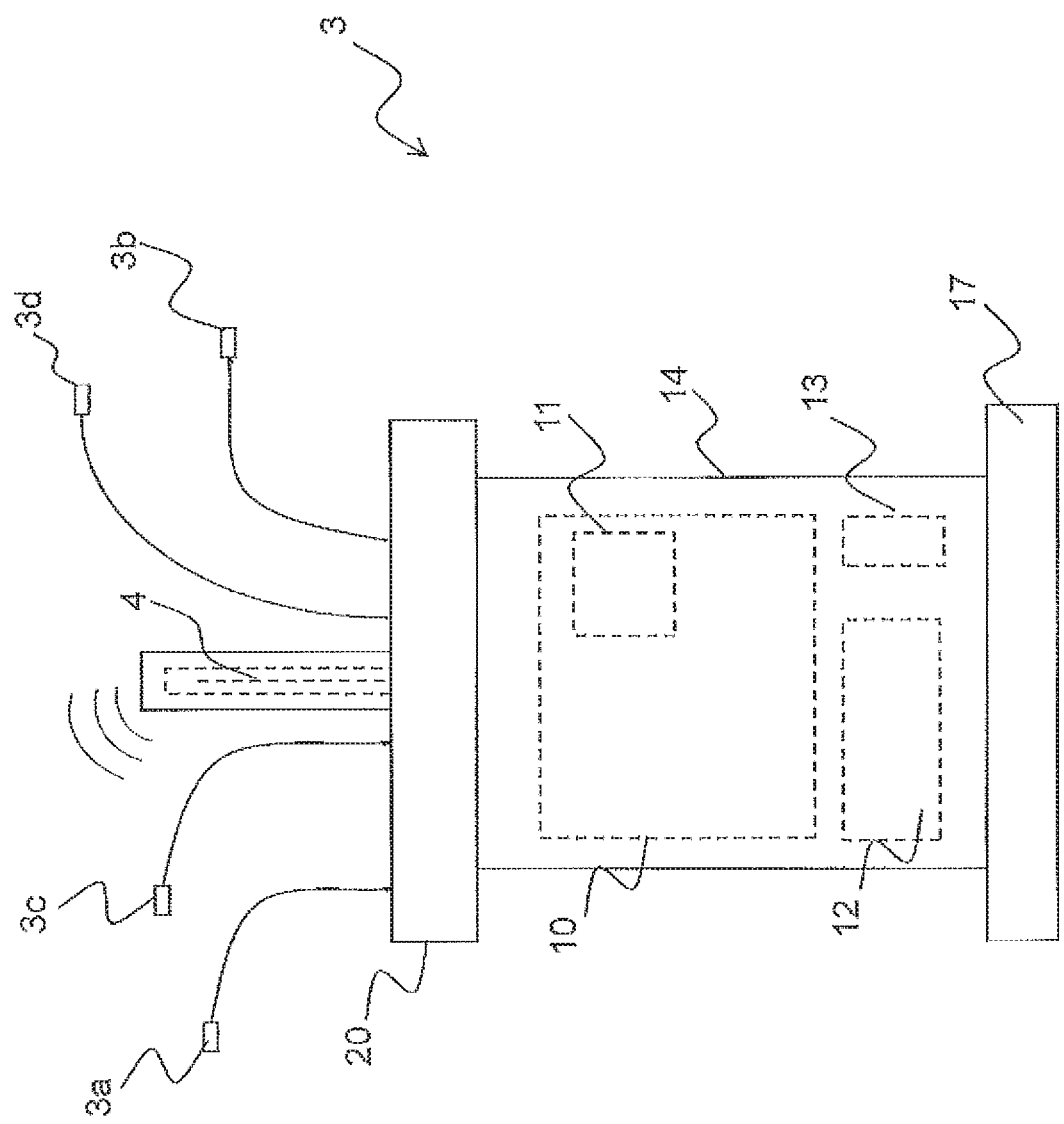
FIG. 2 shows a transparent side view of a transducer of the temperature measuring system according to one embodiment.

With reference to FIG. 1, a schematic view is shown of the architecture of the temperature measuring system 1 inside a sterilisation chamber 2 of an autoclave.

The autoclave is of the type comprising a sterilisation chamber 2 delimited by an enveloping wall and a loading door, preferably hinged or sliding.

The enveloping wall and the loading door are configured to withstand the high temperature and pressure changes that can be generated inside the sterilisation chamber 2 through relevant heating, pressurisation and/or steam injection and suction means (not shown in the figures) driven by a process controller 8 arranged outside the sterilisation chamber 2 and in signal connection with sensor means for monitoring the conditions inside the sterilisation chamber 2 during the sterilisation processes.

The sensor means may comprise one or more pressure sensors (not shown in the figures) and a temperature measuring system 1.

According to an aspect of the present invention, the temperature measuring system 1 comprises at least one temperature transducer 3 that can be positioned inside the sterilisation chamber 2 of the autoclave and at least one receiver device 5 (of the temperature measurements) that can be positioned outside the sterilisation chamber 2 and in signal connection with the process controller 8 of the autoclave.

Inside the sterilisation chamber 2 one or more transducer elements 3 are placed for sampling the temperature inside the severe atmosphere. Each temperature transducer 3 possesses at least two temperature sensors 3a, 3b, 3c, 3d.

Preferably, the metal sheath is of the AISI 316L EN 1.4404 type.

The temperature transducers 3 can be positioned inside the sterilisation chamber 2 in the preferred points, according to the procedures and types of sterilisation treatment to be performed.

The plurality of temperature probes 3a, 3b, 3c, 3d are adapted to generate an analog signal corresponding to the temperature to which they are exposed. The temperature probes 3a, 3b, 3c, 3d can be movable with respect to the transducer housing 14 and connected thereto through signal conductors for transmitting the analog temperature signal.

Each temperature transducer 3 further comprises a (first) transmission antenna 4 connected to the transducer housing 14 and an electronic transduction circuit 10 housed inside the transducer housing 14 and connected to the signal conductors of the temperature probes 3a, 3b, 3c, 3d and to the transmission antenna 4. The electronic transduction circuit 10 is configured to convert the analog temperature signal into a digital temperature signal and transmit it through the transmission antenna 4 to the antenna of a receiver device 5.

The data sent by the antenna 4 are for example the those of the temperature measurement inside the chamber 2, reporting of any malfunctioning, power supply battery running out, data, registry parameters and calibration data.

Each receiver device 5 comprises a (second) reception antenna 6 and an electronic coordination circuit 7, 9 connected to the reception antenna 6 and connectable to the controller 8 of the autoclave. The electronic coordination circuit 7, 9 is configured to receive the digital temperature signal (generated and emitted in the form of radiofrequency by the temperature sensor 3) through the reception antenna 6, provide a control signal as a function of the digital temperature signal and transmit such control signal to the controller 8 of the autoclave.

Thanks to this wireless transmission of the temperature signal from inside the sterilisation chamber 2 to the receiver 5 positioned externally thereto, a flexible temperature measurement is obtained, that can be easily adapted to various forms, quantities, configurations of objects or substances to be sterilised and free from the disadvantages of systems with transmission cables that pass from the inside to the outside of the sterilisation chamber. The reception antennae 6, provided in the receiver devices 5 are placed outside the sterilisation chamber 2, preferably on the top thereof.

The antenna 6 of the receiver device 5 is positioned outside the sterilisation chamber 2 so that it is separate or isolated from the latter through an enveloping wall 18 of the sterilisation chamber 2.

As the enveloping wall 18 is advantageously made of stainless steel and therefore forms a Faraday cage that cannot be penetrated by RF electromagnetic waves, the layer or local wall can be made of radiofrequency-transparent material and shaped so as to form a protuberance or protrusion 19 that projects into the sterilisation chamber 2 and forms an external cavity (with respect to the sterilisation chamber 2) for housing the reception antenna 6. In this way, the reception antenna 6 projects into the internal volume of the sterilisation chamber 2, allowing the reception and transmission of RF signals, but remains isolated from it through the local wall 18.

According to a preferred embodiment, the reception antenna 6 itself is housed in an outer container 15a, projecting into the sterilisation chamber 2. Such outer container 15a forms the aforesaid radiofrequency-transparent local wall but, is resistant to the pressure and temperature inside the sterilisation chamber 2.

The transduction antennae 4 are protected by a case or case made of plastic material that complies with food and healthcare standards and suitable for operation at high temperatures.

The number of transduction antennae 4 that must be located inside the sterilisation chamber 2 varies as a function of the length of the autoclave and the spatial resolution to be obtained, while the position of the transduction antennae 4 on the cross section vary as a function of the shape of the chamber (which may be quadrangular or cylindrical) and the process performed, so as not to interfere with any moving loads.

Preferably, there must be at least two transduction antennae 4 installed and the distance between them must not exceed 1.5 metres. Preferably, the transduction antennae 4 are mutually spaced by 1.25 metres, so as to guarantee the optimal superposition of the transmission electromagnetic fields.

Preferably, the transmission rated power of the signal of the temperature transducer 3 is 5 mW, whereas that of the receiver device 5 is 5 mW. The transmission distance of the signal in the free field is greater than 3 m for both devices.

Each temperature reception antenna 6 is connected to the related receiving module 16, preferably placed outside the sterilisation chamber 2, by means of a coaxial cable.

Each receiving module 16 is in turn connected to a first Master electronic coordination circuit 7, which processes the data and communicates with the process controller 8 through Profibus protocol (Process Field Bus).

Preferably, the first Master electronic coordination circuit 7 handles four receiver devices 5.

In the case in which a larger number of second reception antennae 6 is required and therefore more receiving modules 16, one or more (second) Slave electronic coordination circuits 9 need to be installed which in turn are connected to a maximum of another four receiving modules 16.

The receiving modules 16 can be connected to corresponding Slave 9 and Master 7 coordination circuits through a communication bus CAN-bus (Controller Area Network) or a Profibus field bus (Process Field Bus). Likewise, the Slave circuit 9 communicates in turn with the Master circuit 7 with the same protocol. The Master circuit 7 can be connected to the process controller 8 through a single communication bus, e.g. a CAN-bus or a Profibus field bus (Process Field Bus).

The architecture 1 of the system allows a plurality of second Slave coordination circuits 9 to be connected to a (first) Master circuit 7. Preferably, a Master device 7 can be connected with two Slave devices 9 for a total of twelve transmitters 5 and therefore twelve antennae 6.

Very complex installations can envisage the presence of a second parallel system, complete with all the components mentioned above that is able not to enter into conflict with the main one.

The wireless communication between the transmission element 4 and the reception antennae 6, connected to the receiving module 16, is based on a proprietary transmission protocol.

The packages of temperature data detected by the transducers 3 are transmitted by the related transduction antennae 4 and captured by the reception antennae 6 (one-to-many logic). The system 1 is able to discard identical data by preferring the datum characterised by the best reception. If multiple transduction devices 3 are provided inside the sterilisation chamber 2, the transmission management takes place through time offsets predefined during the initial configuration step, so that the signals are not superimposed and therefore minimising the risk of data loss.

The communication between the antennae 4, 6 is wireless at a specific frequency, preferably in the field of so-called Ultra High Frequencies (UHF). Preferably, the low frequencies used are 868 MHz and 902 MHz. The passage from one frequency to another takes place by intervening on the hardware and reconfiguring the system.

The temperature transducer 3 constitutes one of the fundamental elements of the system. In particular, it performs the functions of temperature acquisition inside the sterilisation chamber 2 and wireless data transmission.

The electronic circuitry is housed inside a protective polyether ether ketone (PEEK) case. The case 14 houses internally the electronic transduction circuitry 10, the primary battery 12, the auxiliary battery 13, the connection cables between the electronic transduction circuit and the batteries, the communication antennae 4 and the connections between the temperature and the electronic circuit 10.

To guarantee access to the elements internal to the temperature transducer 3 (e.g. for replacing the batteries), the case 14 is made of two parts fixed together by screws made of the same material.

To protect against possible infiltrations of fluid into the case, between the two half-parts a gasket is interposed, made of translucent silicone for applications in the healthcare and food environment, with a hardness of 70 Sh A, to guarantee a better seal during all operating conditions.

In optimal clamping conditions an IP68 protection rating according to EN 60529 is achieved.

Externally, the case may be provided with elements that allow the fixing thereof to carriages and rotating baskets.

The arrangement of the components inside the case guarantees easy manoeuvring for replacing the batteries.

The entry point of each probe is preferably provided with an appropriate sealing O-Ring made of FKM Viton, a compatible material with FDA 21 CFR 177.2600.

The antenna 4 of the transducer, which is used for communication with the receiver devices 5 present outside the sterilisation chamber, is housed inside the protective case but is preferably not integrated into the electronic circuitry 10. The connection between the antenna 4 and the circuit 10 takes place through a specific connector.

All the stored data, with the exception of those for temporary use (e.g. the data stored temporarily for the acquisition and/or definition of the measurements), are saved on a non-volatile memory and are therefore also maintained in the absence of electrical power supply thereto.

The reception of the signal sent by the transducer 3 is managed by the receiver devices 5, each of which is comprised by at least one reception antenna 6 and the related receiving electronic circuit 16. The functions performed by the electronic module 16 relate to the processing and decoding of the radio signal, sampling of the datum and transmission of the datum to the device to which they are connected (i.e. Master 7 or Slave 9).

Figure 3:
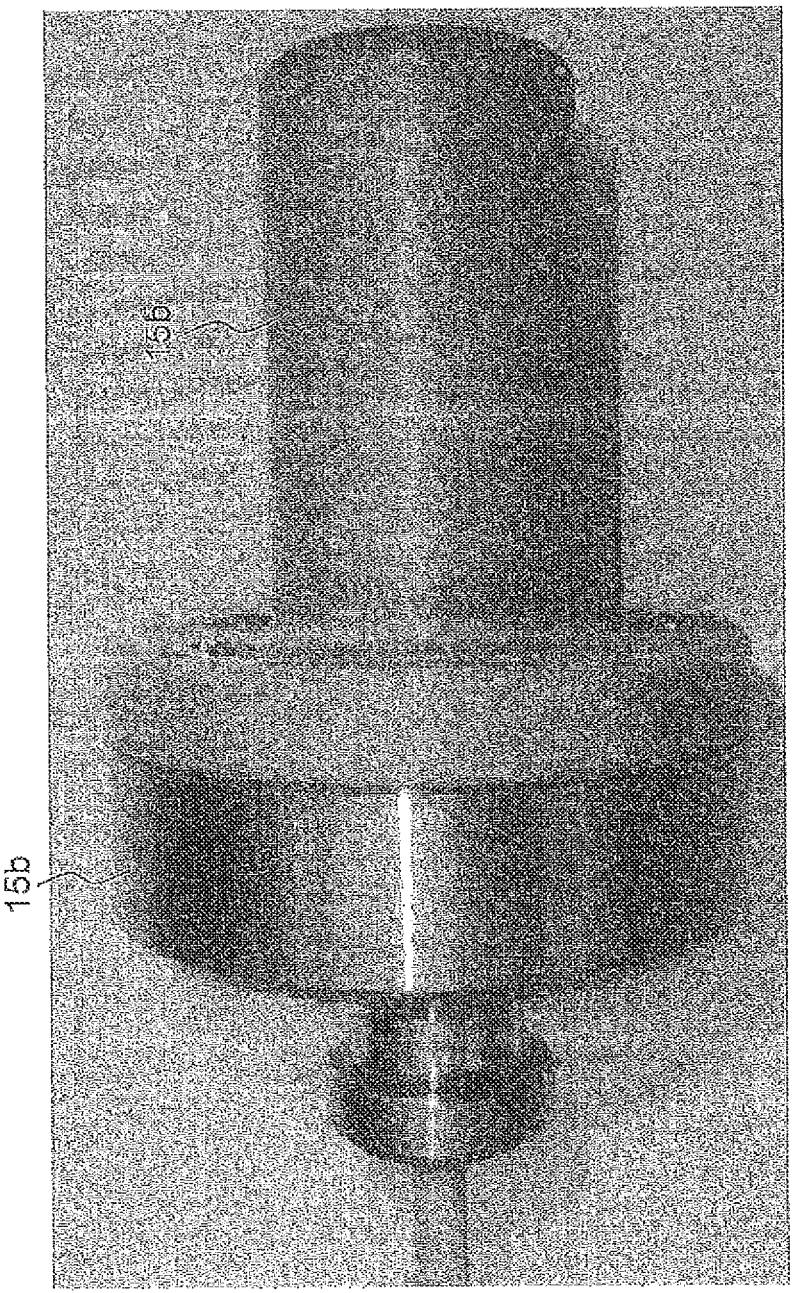
FIG. 3 shows an antenna of the measurement receiver.
Figure 4:
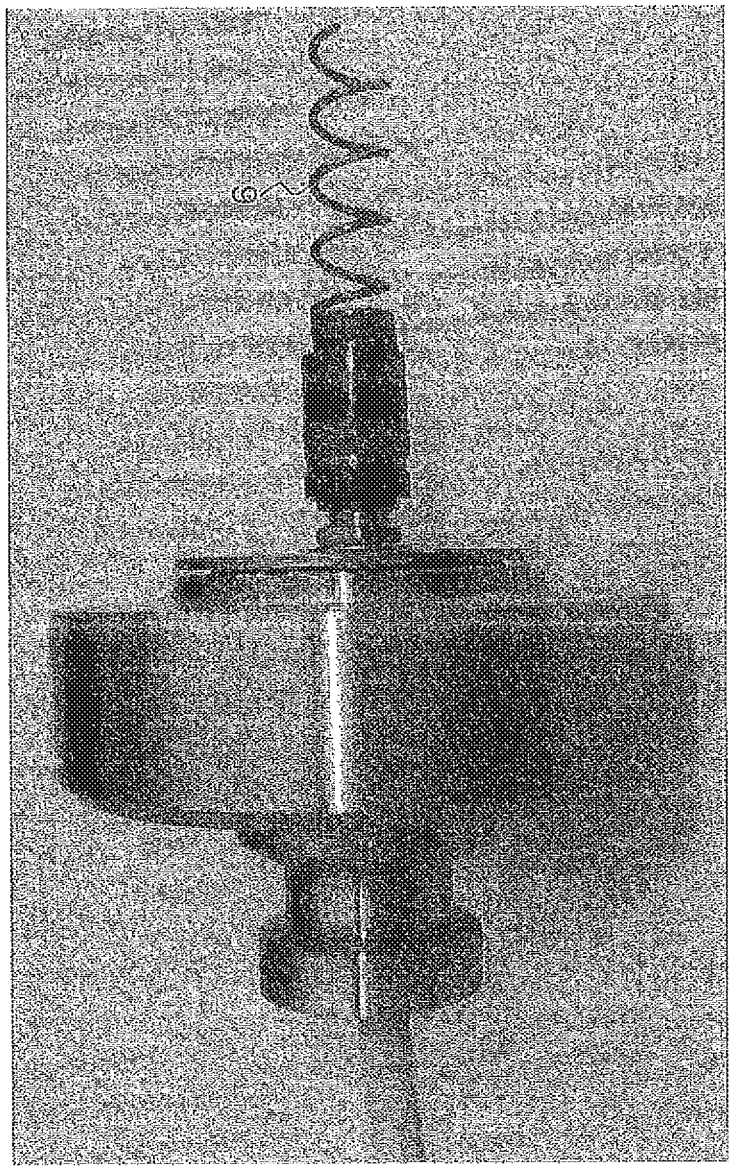
FIG. 4 shows the antenna of FIG. 3 disassembled.

The electronic module 16 is also configured to send commands (e.g. on and/or off) to an activation device 11 provided inside each temperature transducer 3 of the sterilisation chamber 2. The signals generated by the electronic module 16 are transmitted by the antenna 6 of the receiver device 5 and received by the antenna 4 of each temperature transducer 3. The reception antenna 6 is protected from the severe environmental conditions by a protective case, preferably cylinder shaped made in two parts, shown in FIG. 3. Preferably, the part 15a of the case that protects the antenna 6 is made of high resistance plastic materials whereas the lower part of the case 15b is made of stainless steel (316L). The two parts 15a, 15b of the protective case are held together with steel screws. Preferably, the part 15a of the outer container of the antenna 6 is made of polyether ether ketone (PEEK). The antenna 5 visible in FIG. 4 is of the helical type.

The presence of the protective element 15a, 15b implies an alteration of the transmission carrier frequency, such as to make an antenna available on the market incompatible with the present application.

To solve such problem, the antenna 6 is calibrated considering the frequency variation due to the presence of the protective case 15a, 15b, of the containers and of the coaxial cable, compensating for such variation so as to be repositioned at the transmission frequency that guarantees the best communication efficiency inside the chamber 2.

The calibration activity is performed outside the sterilisation chamber 2, arranging the assembled elements on a metal wall that simulates the environment on which they will operate, and appropriately changing the length of the coils until reaching the maximum radiated power peak, which is distributed according to a Gaussian curve. The antenna 6 can be calibrated in dual-band mode for promoting installations for European and North American users or for particular applications. The functions of the Master device 7 include managing and coordinating the receivers 5, receiving the acquired data, communicating with the process controller 8 of the autoclave and managing any Slave boards 9, when provided. The electronic circuitry of the master 7 is contained inside a container made of plastic material and with protective rating IP67, positioned in the technical compartment of the autoclave. The Master device 7 is also provided with an LCD display for its initial configuration.

Any Slave circuits 9, used whenever the number of receiving elements is over 4, are similar to the Master coordination circuit 7 described above. However, it only has the function of managing additional receivers 5 and transferring the read data acquired by it to the Master device 7, which in turn sends them to the process controller. The communication with the device takes place through CAN-Open communication protocol.

The Master coordination circuit 7 is preferably powered by a 24V/1 A external source. It is also possible to connect the system under UPS, even if this is not strictly necessary as, in the event of a voltage drop, the process controller interrupts the cycle, without the need to keep the temperature acquisition active.

The electronic transduction circuit 10, provided inside the transducer 3, is powered by a main battery 12 preferably of the D type with lithium polymer technology, with rated voltage of 3.6V adapted to allow autonomous and wireless electrical power supply of the primary electronic circuit. The main battery 12 is interchangeable.

The endurance of the battery 12 varies as a function mainly of the daily use and the operating temperatures. However, an endurance of 8 months is possible, considering operation of about 8 h/day. In the event of malfunctioning or lack of the primary power supply, an emergency auxiliary battery 13 automatically intervenes. It will have an endurance less than that of the main battery 12 as it must allow the sterilisation cycle in progress to be concluded. Indicatively, its endurance is limited to 24/36 hours. The level of charge of the primary battery 12 is displayed by the process controller 8 of the autoclave during operation. The process controller 8 reports the temperature transducers 3 whose primary battery 12 charge has run out and are only active by means of the auxiliary battery 13. In this way, the operator is informed before the start of the cycle that the devices not covered by the primary battery 12 may be excluded from the registrations envisaged by the sterilisation cycle.

In order to notably increase the endurance of the batteries of the temperature transducers 3, there is an activation device 11 inside them that can implement an energy saving mode that allows the electronic transduction circuit 10 to be switched on only when needed, e.g. when the acquisition of data is required, leaving it off in all the other conditions.

Preferably, the activation device 11 can be placed inside the electronic coordination circuit 10. The activation device 11 remains powered with negligible consumption levels for the purpose of battery endurance.

It is able to switch on the electronic transduction circuit 10 when the elements of the measuring system start the communication, i.e. when it is inside the sterilisation chamber and the process controller 8 of the autoclave starts the step immediately prior to the preparation of the sterilisation cycle, or when it is in the calibration step, close to a specific calibration interface.

Figure 5:
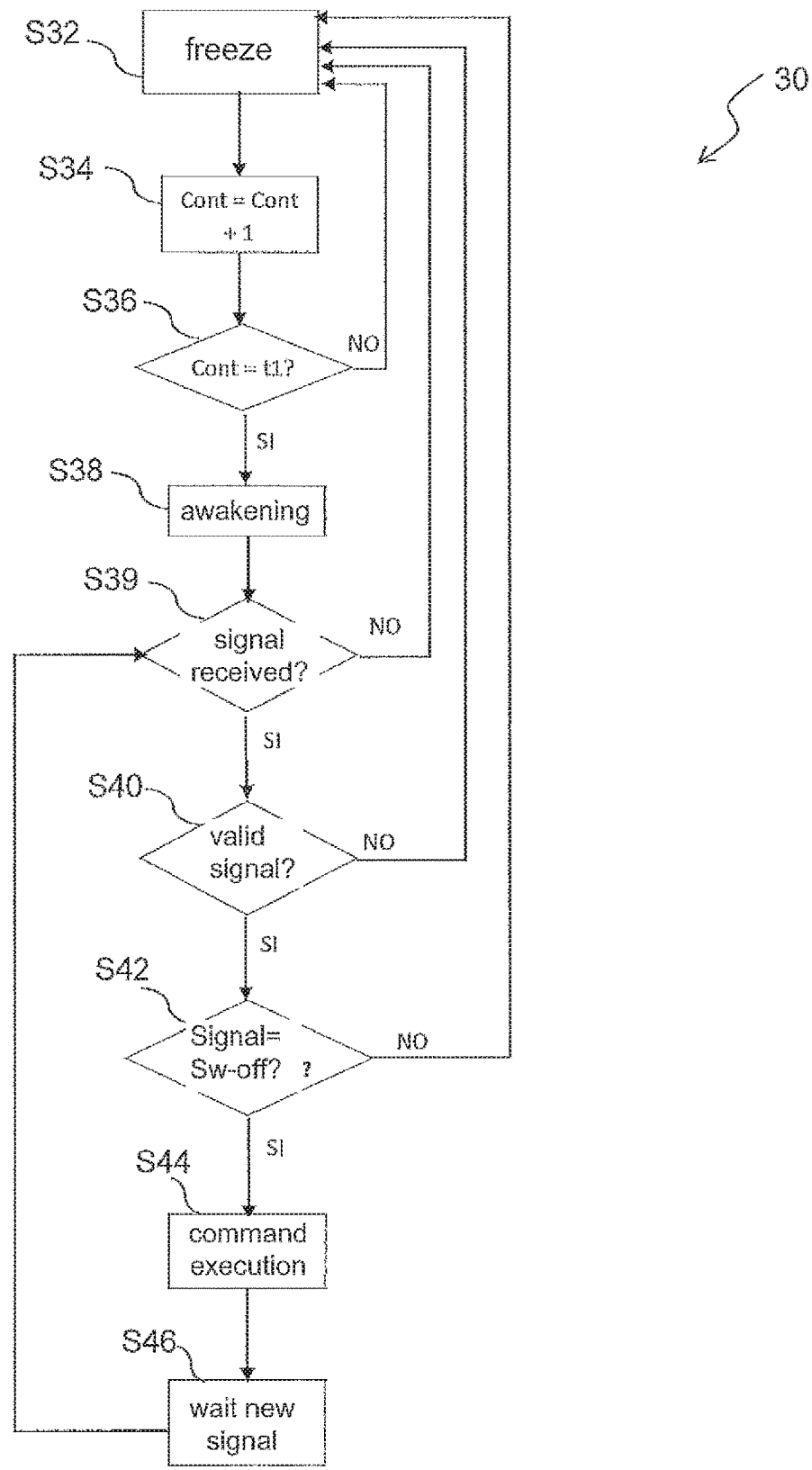
FIG. 5 shows a flow diagram illustrating the steps of the activation device.

The various operating steps of the activation device 11 are schematically illustrated in the flow diagram 30 of FIG. 5.

In a preliminary step, not shown in the diagram 30, the meter "cont" is initialised and set equal to zero.

In step S32, the activation device 11 is in a reduced energy consumption status (or "deep sleep"), in which the energy consumption is almost reduced to zero (and the electronic transduction circuit 10 and all the other components of the temperature transducer 3 are off).

After a time interval t1 (step S36), the activation device 11 is activated in signal reception mode (S38, "wake-up") for a second time interval t2 (preferably, t2 is a period of less than 300 μs). Preferably, the time t1 is equal to 3 seconds, i.e. the activation device 11 is activated every 3 seconds (t1) for a period of less than 300 μs (t2). During the time interval t2, the activation device verifies whether it has received a valid command signal (step S40).

If the activation device 11 does not receive any signal (step S39) or if the received signal is not valid (S40), it returns to the initial status S32, repeating the cycle.

In other words, in steps S39 and S40, the activation device 11 checks if anyone is interrogating it for a time interval t2 (sending of a valid command signal).

Vice versa, if in the step S40 a valid signal is received, step S42 begins, in which it is verified whether the signal received is for switching off ("power-off"), i.e. switching off the electronic activation device 11.

If in the short time in which the activation device 11 remains active (steps S38, S40, S42) it recognises a valid switching on signal, the electronic activation device 11 will switch on the electronic transduction circuit 10 and all the other components of the transduction device 3, it will perform the command received (step S44).

Subsequently, it moves onto the new signal reception mode (S46) and waits for further commands until the switching off command is received, which brings it back again to the reduced energy consumption status. In the steps in which the electronic transduction circuit 10 is active and supplied by the primary battery 12, it transmits the temperature measurements detected by the sensors 3a, 3b, 3c, 3d, from the antenna 4 of the transducer 3 to the antennae 6 of the receiver devices 5 located outside the sterilisation chamber 2.

This operating mode, implemented by the power supply device 11, allows energy savings 4,000 times lower with respect to normal continuous operation to be obtained.

In the event of interferences from external RF signals, the activation device 11 keeps the electronic transduction circuit 10 off, allowing further energy savings.

The system 1 is able to transmit the data within a completely closed chamber, having a cylindrical or quadrangular shape, made of stainless steel and with mirror-polished surfaces.

The communication between the Master electronic surface 7 and the process controller 8 of the autoclave takes place when one or more of the following circumstances arises:

Start-up of the apparatus and/or of the process controller. It is used to start the Wireless system configuration procedure (through a specific "query"). During such operation, the number of input analog channels is defined (however, the channels may then not be effectively used) and at the same time the Master device provides the process controller with the identification data of the connected transmitting elements and of the temperature sensors connected thereto.

From the start to the completion of the cycle: the Master element 7 must guarantee transmission to the process controller 8 of the updated values for the entire duration of the work cycle.

On condition: following intervention of the self-diagnostic function of a transmitting element 4 in connection with the receiving element 6, the relative messages, warnings or alarms must be immediately transferred to the process controller. Should the self-diagnostic function be implemented also on receiving modules, they must provide to send data to the process controller 8 according to the same modes as the Master circuit 7.

It is possible that measuring systems 1 are used on various autoclaves arranged close to each other. Even if the body of the autoclave acts as a Faraday cage and confines the wireless transmissions to the inside of it, interference caused by nearby devices is possible. To guarantee communication between the devices provided in the chamber only, the system is designed not to consider signals that have power less than a predefined threshold, which is reasonably typical of a device located outside the machine. The minimum threshold value that is required to discriminate the signals must be defined before the equipment is used (i.e. before starting the measuring cycle).

The temperature measuring system 1 thus forms an integral part of the sterilisation process driven by the controller 8 also as a function of the temperatures measured and transmitted in real time.

As the wireless transmission of signals between the transmission 4 and reception antennae 6 is confined within a structure that is completely shielded from the external space, it is possible to avoid having to comply with the strict legislation on data transmission powers and stronger, more reliable signals can be used.

Preferably, the electronic transduction circuit 10 is connected to a local memory that comprises an electronic data-sheet containing a calibration certificate and configured to periodically perform a self-calibration cycle for each temperature probe 3a, 3b, 3c, 3d connected.

A monitoring means is also provided for monitoring the residual charge of the primary battery 12, configured to monitor the residual charge of the primary battery 12 at every start of a temperature measurement cycle and, if the residual charge is less than a reference value for the transmission time set, such battery monitoring means prevents the start of the process and/or generates an alarm signal and/or a (primary and secondary) battery replacement request signal. Preferably this monitoring means is realised through the electronic transduction circuit 10.

The above description of the "transmission" antenna 4 (provided in the temperature transducer 3) and the "reception" antenna 6 (provided in the receiving device) relates to the transmission of the temperature signal measured inside the sterilisation chamber 2 and transmitted to the reception antenna 6. However, the "reception" antenna 6 is also configured to be able to "send" command signals to the antenna 4 of the transducer 3, e.g. activation and/or off commands of the electronic activation device 11 and other service commands. In that case, the (temperature) transmission antenna 4 of the transducer 3 is also able to "receive" commands and signals from the antenna 6.

The present invention also relates to a reception antenna 6 for a receiver 5, positionable outside a sterilisation chamber 2, as described above.

The invention claimed is:

1. A system for measuring temperature in a sterilization autoclave, comprising:
   at least one temperature transducer positionable inside a sterilization chamber of the autoclave; and
   at least one receiver positionable outside the sterilization chamber,
      wherein the at least one receiver comprises:
         a reception antenna, and
         a receiving electronic circuit connected to the reception antenna and connectable with a process controller of the autoclave, wherein said receiving electronic circuit is configured to receive a digital temperature signal through the reception antenna, provide a control signal as a function of the digital temperature signal and transmit the control signal to the process controller,
      wherein the at least one temperature transducer comprises:
         a hermetically closable transducer housing,
         temperature probes adapted to generate an analog temperature signal corresponding to a temperature to which the temperature probes are exposed, the temperature probes being movable with respect to the transducer housing and connected thereto through signal conductors for transmitting the analog temperature signal,
         a transmission antenna connected to the transducer housing,
         an electronic transduction circuit housed inside the transducer housing and connected to the signal conductors and to the transmission antenna, wherein the electronic transduction circuit is configured to convert the analog temperature signal into the digital temperature signal and transmit the digital temperature signal through the transmission antenna to the receiver, and
         a primary battery to provide an autonomous electric power supply of the electronic transduction circuit, and
      wherein the reception antenna of the receiver is configured to transmit signals at two or more different frequencies.

2. The system according to claim 1, wherein the reception antenna of the receiver is housed inside an outer container made of polyether ether ketone.

3. The system according to claim 1, wherein the reception antenna is a dual-band reception antenna, able to transmit and receive signals at least at 868 MHz and 902 MHz frequencies.

4. The system according to claim 1, further comprising a transmission frequency selector of the reception antenna.

5. The system according to claim 1, wherein the reception antenna is a helical type antenna.

6. The system according to claim 1, wherein the reception antenna is located outside the sterilization chamber, housed in a protuberance or column that projects into an internal volume of the sterilization chamber, allowing reception and transmission of RF signals, but remaining isolated therefrom through a local wall of the sterilization chamber.

7. The system according to claim 1, wherein the at least one temperature transducer are a plurality of temperature transducers, and wherein the at least one receiver are a plurality of receivers.

8. The system according to claim 7, wherein reception antennae of the plurality of receivers are placed at a mutual distance of 1.25 m.

9. The system (1) according to claim 7, wherein reception antennae of the plurality of receivers are arranged on the roof of the sterilization chamber.

\* \* \* \* \*